(12) United States Patent
Chen et al.

(10) Patent No.: US 11,497,496 B2
(45) Date of Patent: Nov. 15, 2022

(54) SURGICAL INSTRUMENT HAVING INTERLOCKING MECHANISM

(71) Applicant: REACH SURGICAL, INC., Tianjin (CN)

(72) Inventors: Xiaoqiang Chen, Tianjin (CN); Zhenzhen Xu, Tianjin (CN)

(73) Assignee: REACH SURGICAL, INC., Tianjin (CN)

( * ) Notice: Subject to any disclaimer, the term of this patent is extended or adjusted under 35 U.S.C. 154(b) by 50 days.

(21) Appl. No.: 17/356,594

(22) Filed: Jun. 24, 2021

(65) Prior Publication Data

US 2021/0315572 A1 Oct. 14, 2021

Related U.S. Application Data

(63) Continuation of application No. 16/407,392, filed on May 9, 2019, now Pat. No. 11,071,542.

(51) Int. Cl.
*A61B 17/068* (2006.01)
*A61B 17/072* (2006.01)
*A61B 17/29* (2006.01)

(52) U.S. Cl.
CPC .. *A61B 17/072* (2013.01); *A61B 2017/07257* (2013.01); *A61B 2017/07271* (2013.01); *A61B 2017/07285* (2013.01); *A61B 2017/2946* (2013.01)

(58) Field of Classification Search
CPC ..... A61B 17/072; A61B 17/068; A61B 17/29; A61B 2017/2946; A61B 2017/2901
USPC .................................................. 227/175.2
See application file for complete search history.

(56) References Cited

U.S. PATENT DOCUMENTS

| | | | | |
|---|---|---|---|---|
| 5,465,895 A * | 11/1995 | Knodel | ............ | A61B 17/07207 227/176.1 |
| 5,626,587 A * | 5/1997 | Bishop | ............... | A61B 17/0682 227/175.1 |
| 6,273,200 B1 * | 8/2001 | Smith | ..................... | B25B 21/00 173/216 |
| 6,523,442 B2 * | 2/2003 | Lehnert | .................. | B25B 21/00 173/176 |
| 6,676,557 B2 * | 1/2004 | Milbourne | ............. | B23Q 5/142 173/178 |
| 6,796,921 B1 * | 9/2004 | Buck | ....................... | B25F 5/001 173/47 |
| 8,398,673 B2 * | 3/2013 | Hinchliffe | ............ | A61B 17/295 606/205 |
| 8,616,431 B2 * | 12/2013 | Timm | ..................... | A61B 34/30 227/178.1 |
| 8,733,612 B2 * | 5/2014 | Ma | .................... | A61B 17/07207 227/175.2 |

(Continued)

*Primary Examiner* — Gloria R Weeks
(74) *Attorney, Agent, or Firm* — ArentFox Schiff LLP; Michael Fainberg

(57) ABSTRACT

Disclosed is a surgical instrument having an interlock mechanism, and the surgical instrument includes a handle portion having a handle housing; an elongated body, defining a longitudinal axis of the instrument; an end effector, arranged on distal portion of the elongated body for operating tissues; a rotatable sleeve, circumferentially fixed with proximal portion of the elongated body and provided with a plurality of teeth; a rotatable knob, operatively to be reciprocated along the longitudinal axis; and an articulation gear assembly including an annular gear and a planet gear assembly.

18 Claims, 10 Drawing Sheets

(56) References Cited

U.S. PATENT DOCUMENTS

| | | | | |
|---|---|---|---|---|
| 2004/0084195 A1* | 5/2004 | Ullah | ............. | B23Q 5/043 173/216 |
| 2012/0234893 A1* | 9/2012 | Schuckmann | ... | A61B 17/07207 227/175.2 |
| 2014/0239040 A1* | 8/2014 | Fanelli | ............. | A61B 17/07207 227/175.2 |
| 2014/0263545 A1* | 9/2014 | Williams | ......... | A61B 17/07207 227/175.2 |
| 2014/0339286 A1* | 11/2014 | Motooka | .......... | A61B 17/07207 227/175.2 |
| 2015/0053738 A1* | 2/2015 | Morgan | ............... | A61B 17/105 227/175.1 |
| 2015/0272581 A1* | 10/2015 | Leimbach | ........ | A61B 17/07207 227/175.2 |
| 2016/0030043 A1* | 2/2016 | Fanelli | ............. | A61B 17/07207 227/175.1 |

* cited by examiner

SURGICAL INSTRUMENT HAVING INTERLOCKING MECHANISM

CROSS-REFERENCE TO RELATED APPLICATIONS

This application is a continuation of U.S. patent application Ser. No. 16/407,392, filed on May 9, 2019, which is hereby incorporated by reference in its entirety.

FIELD

The present invention relates to the field of medical instruments, and particularly to a surgical instrument having an interlock mechanism.

BACKGROUND

Endoscopic surgical instruments provide a patient with minute surgical wound and, good surgical effects, so it can greatly alleviate the patient from surgical pains.

Typical surgical instrument includes an operating handle, an elongated portion, and an end effector. The operating handle includes a stationary handle to be grasped by an operator, and the distal portion of the operating handle (the portion of the operating handle closer to the operator is referred to as a proximal portion, and the portion of the operating handle farther from the operator is referred to as a distal portion) is connected with the end effector through the elongated portion.

Currently, the surgical instrument is provided with three functions which are articulation, rotation and closing to thereby adjust an operating angle and an operating position of the end effector. For providing implementing safety of the instrument during surgery, rotation of the instrument shall not be allowed during articulation thereof, articulation shall not be allowed during rotation, and neither articulation nor rotation shall be allowed after the instrument is closed, so as to improve the operability of the surgical instrument, reducing surgical risks during surgery caused by improper operations.

The surgical instrument shall be provided with a set of locking assemblies to interlock the surgical instrument among the three modes above. However, typically the surgical instrument is generally locked in a damping manner, that is, the surgical instrument is locked using a damping force provided by a damping module so that the surgical instrument is locked in a certain functional mode.

However, for the surgical instrument to be locked by the locking assemblies in damping manner, if a driving force of the surgical instrument is beyond a certain threshold, the damping force provided by the damping module will be invalidated so that a risk may tend to occur during surgeries caused by improper operations, degrading the safety performance of the surgical instrument.

SUMMARY

The invention provides a surgical instrument having an interlock mechanism, so that the surgical instrument can be operated stably, improving the safety performance of the surgical instrument.

In order to attain the object above, the invention provides the following technical solutions:

A surgical instrument includes: a handle portion having a handle housing; an elongated body, defining a longitudinal axis of the instrument; an end effector, arranged on distal portion of the elongated body for operating tissues; a rotatable sleeve, circumferentially fixed with proximal portion of the elongated body and provided with a plurality of teeth; a rotatable knob, operatively to be reciprocated along the longitudinal axis, where the rotatable knob is provided with a plurality of teeth for operatively engaged with the teeth of the rotatable sleeve in distal position thereof; and an articulation gear assembly including an annular gear and a planet gear assembly, where the annular gear that is rigidly amounted with the rotatable knob, and operatively engaged with the planet gear when the rotatable knob is operated in proximal position thereof.

In some embodiments, the surgical instrument further includes a driving screw rigidly connected with a sun gear of the articulation gear assembly; where the driving screw includes a thread section that is engaged with a driving rod assembly coupled to the end effector.

In some embodiments, the thread section of the driving screw is provided with at least two opposing threads that are engaged with respective driving rods of the driving rod assembly, such that when the rotatable knob is operated in proximal position thereof, rotating the rotatable knob articulates the end effector.

In some embodiments, the surgical instrument further includes a locking assembly including at least one slide member and a lockout gear; where the slide member is arranged between the rotatable knob and the handle housing, and axially fixed with the rotatable knob, so as to be reciprocated with the rotatable knob for being operatively engaged with the lockout gear; and the slide member is circumferentially fixed with the handle housing; and the lockout gear is rigidly mounted at a proximal portion of the elongated portion.

In some embodiments, the slide member is axially fixed in the rotatable knob and configured to be rotatable with respect to the rotatable knob.

In some embodiments, the rotatable knob further includes an annular slot configured to receive the slide member, allowing the slide member to move circumferentially therein.

In some embodiments, an elongated slot is arranged in the distal portion of the handle housing of the handle portion to prevent the slide member from moving circumferentially.

In some embodiments, the rotatable knob is provided with two, three, or four slide members that are evenly spaced in the circumferential direction thereof.

In some embodiments, the handle portion further includes a stationary handle and a closure trigger; and the closure trigger is pivotally mounted on the handle housing, and connected with a closure mechanism arranged in the handle housing, configured for actuating the elongated portion through the closure mechanism to reciprocate for opening or closing the end effector.

In some embodiments, the handle portion further includes a closure lockout assembly rigidly engaged with the closure mechanism; and when the closure trigger is closed, the closure lockout assembly is operatively pushed distally by the closure mechanism.

In some embodiments, the closure lockout assembly is arranged as a safety sheet arranged between the lockout gear and the articulation gear assembly; and as the safety sheet is moving distally, the safety sheet pushes the lockout gear to move distally; or as the safety sheet is moving distally, the safety sheet pushes the lockout gear and the slide member to move distally.

In some embodiments, the safety sheet is structured integral to the articulation gear assembly.

In some embodiments, the safety sheet is arranged as an annular sheet, the outer diameter of which is greater than the outer diameter of the lockout gear.

In some embodiments, the surgical instrument further includes a locking assembly including a slide member and a lockout gear; where the slide member is arranged between the rotatable knob and the handle housing, and axially fixed with the rotatable knob, for being reciprocated with the rotatable knob to be operatively engaged with the lockout gear; the slide member is circumferentially fixed with the elongated portion; and the lockout gear is fixedly mounted in the handle housing.

In some embodiments, the slide member is fixedly sleeved circumferentially on a proximal portion of the elongated portion; and a flange is arranged on a distal portion of the slide member to be snap-fit engaged with the rotatable knob.

In some embodiments, a plurality of teeth are arranged on a proximal portion of the slide member, and as the slide member is moved to the proximal end, the slide member is operatively engaged with the lockout gear.

In some embodiments, the lockout gear is fixedly arranged on the distal portion of the handle housing of the handle portion.

In some embodiments, the handle portion further includes a rotatable sleeve arranged on a distal portion thereof, and rigidly connected with the elongated portion;

where the rotatable knob is operatively engaged with the rotatable sleeve; and a plurality of teeth are arranged respectively on the rotatable sleeve and the rotatable knob, through which the rotatable knob is operatively engaged with the rotatable sleeve.

BRIEF DESCRIPTION OF THE DRAWINGS

In order to make the technical solutions according to the embodiments of the invention more apparent, the drawings to which reference is to be made in the description of the embodiments will be introduced below in brief, and apparently the drawings to be described below illustrate only some embodiments of the invention, and based upon the drawings here, other drawings will occur to those ordinarily skilled in the art without any inventive effort.

DETAILED DESCRIPTION OF THE EMBODIMENTS

The technical solutions according to the embodiments of the invention will be described below clearly with reference to the drawings in the embodiments of the invention, and apparently the embodiments to be described below are only a part but not all of the embodiments of the invention. Based upon the embodiments here of the invention, all the other embodiments which can occur to those ordinarily skilled in the art without any inventive effort shall fall into the scope of the invention.

In the respective embodiments of the invention, the term "distal" refers to the portion of the surgical instrument that is farther from the operator, and the term "proximal" refers to the portion of the surgical instrument that is closer to the operator.

Figures 1, 2, 3:
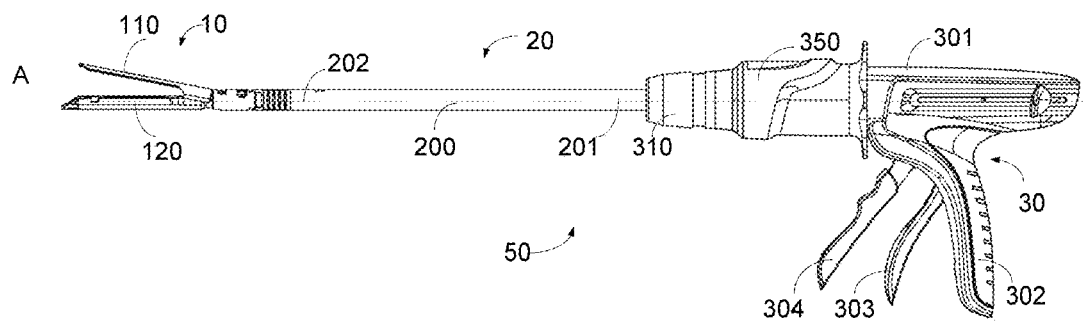
FIG. 1 is a schematic structural diagram of a surgical instrument according to an embodiment of the invention.
FIG. 2 is a schematic structural diagram of the surgical instrument at a rotation position according to the embodiment of the invention.
FIG. 3 is a schematic structural diagram of the surgical instrument at an articulation position according to the embodiment of the invention.

It is provided in one embodiment of the invention a surgical instrument having an interlock mechanism, particularly as shown in FIG. 1, the surgical instrument 50 of the embodiment of the invention includes an end effector 10, an elongated portion 20, and a handle portion 30, where a proximal end 201 of the elongated portion 20 is in connection with the handle portion 30, and a distal end 202 thereof is connection with the end effector 10. The end effector 10 includes an anvil assembly 110 and a cartridge assembly 120, and the anvil assembly 110 is pivotally mounted on the cartridge assembly 120; The handle portion 30 includes a handle housing 301, a handle 302, a closure trigger 303, and a firing trigger 304, where the closure trigger 303 is adapted to drive the anvil assembly 110 through a closure mechanism to pivot relative to the cartridge assembly 120 so as to thereby close or open the end effector 10 (as detailed below); and after the end effector 10 is closed, the firing trigger 304 is adapted to fire a plurality of staples arranged in the cartridge assembly 120 for stapling tissue. The surgical instrument according to any one of the embodiments of the invention is provided with functions of articulation and rotation, i.e. the end effector 10 can be performed to rotate and/or articulate based on the position of the target tissue during surgery, such that the end effector 10 can be adjusted to get a better position to clamp the tissue for cutting and stapling, or other operations. Implementations of the surgical instrument according to the embodiments of the invention for performing rotation and/or articulation will be described below in details with reference to the drawings.

It shall be noted that the surgical instrument according to any one of the embodiments of the invention will not be limited to the linear cut stapler as described in the specification, more specifically, the end effector 10 of the surgical instrument according to any one of the embodiments of the invention will not be limited to the structure of the linear cut stapler as described above, e.g., the anvil assembly 110 and the cartridge assembly 120. Moreover the end effector 10 of the surgical instrument according to any one of the embodiments of the invention can alternatively be configured to perform other surgical operations, e.g., a forceps, a scissor, jaw members of an electrosurgical surgical instrument, etc.

Rotation Mechanism

As illustrated in FIG. 1, the surgical instrument 50 according to the embodiment of the invention includes a rotation mechanism, and particularly, the rotation mechanism includes a rotatable sleeve 310 arranged on the distal portion of the handle housing 301, and the distal portion thereof is circumferentially fixed with the proximal portion of an elongated body housing 200 of the elongated portion 20. Rotating the rotatable sleeve 310, the elongated body housing 200 and the end effector 10 that coupled with the distal end of the elongated body housing 200 can be actuated to rotate accordingly, performing the rotation function of the surgical instrument 50 according to the embodiment. Preferably the rotatable sleeve 310 is rigidly connected with the elongated body housing 200, for example, the rotatable sleeve 310 can be fixed with the elongated body housing 200 in any feasible rigid connection manner, e.g., in a snap-fit manner.

Articulation Mechanism

Referring to FIG. 1 to FIG. 4, the surgical instrument 50 according to any one of the embodiments of the invention further includes a rotatable knob 350 arranged on the handle housing 301, and an articulation mechanism, operatively to be engaged with the rotatable knob 350, adapted to articulate the end effector 10. Particularly the articulation mechanism includes an articulation gear assembly 360, a driving screw 320 connected with the articulation gear assembly 360, and a driving rod assembly 330 arranged in the elongated body housing 200, which is connected respectively with the driving screw 320 and the end effector 10. Rotating the rotatable knob 350, the articulation gear assembly 360 can be actuated accordingly so as to articulate the end effector 10.

Figure 4:
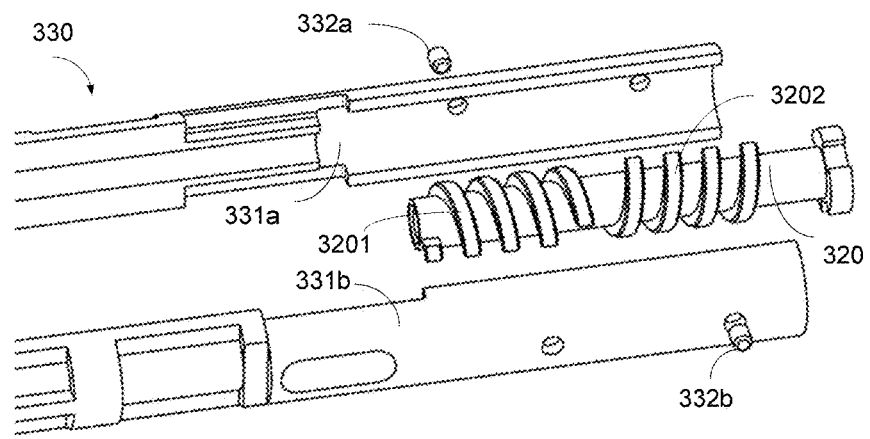
FIG. 4 is a schematic structural diagram of engagement between a driving screw and a driving rod assembly in the surgical instrument according to the embodiment of the invention.

Particularly, in an implementation of the articulation mechanism in the surgical instrument 50 according to any one of the embodiments of the invention, as illustrated in FIG. 4, two thread sections with opposing rotation directions are arranged on the driving screw 320, for example, a first thread section 3201 and a second thread section 3202 are arranged on the driving screw 320, where the rotation direction of the first thread section 3201 is opposite to that of the second thread section 3202. The driving rod assembly 330 includes a first driving rod 331a and a second driving rod 331b, where the first driving rod 331a is engaged with the first thread section 3201 through a first pin 332a, and the second driving rod 331b is engaged with the second thread section 3202 through a second pin 332b; or vice versa. In operation, the driving screw 320 can be rotated to actuate the first driving rod 331a and the second driving rod 331b to move in opposed directions to thereby actuate the end effector 10 arranged on the distal end thereof to articulate.

Figure 5:
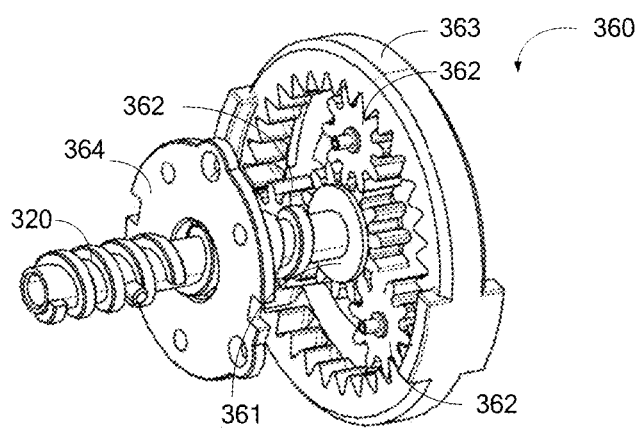
FIG. 5 is a schematic structural diagram of engagement between an articulation gear assembly and the driving screw in the surgical instrument according to the embodiment of the invention.

Preferably, in the embodiment above, the articulation gear assembly 360 is configured as a planet gear train to perform transmission. As illustrated in FIG. 5, for example, the articulation gear assembly 360 includes a sun gear 361, a plurality of planet gears 362, an annular gear 363, and a carrier 364. Preferably in this embodiment, three planet gears 362 are set, and the annular gear 363 is fixed in the rotatable knob 350. More specifically, the annular gear 363 is axially fixed with the rotatable knob 350, and is operatively to rotate together with rotation of the rotatable knob 350. Furthermore the sun gear 361 is rigidly connected with the proximal end of the driving screw 320, and the carrier 364 is fixed in the handle housing 301. Rotation of the annular gear 363 may actuate the sun gear 361 to rotate, and since the sun gear 361 is rigidly connected with the proximal end of the driving screw 320, the driving screw 320 is rotated as well with the rotation of the sun gear 361, so that the first driving rod 331a and the second driving rod 331b are actuated to move in opposed directions to thereby articulate the end effector 10.

It shall be noted that articulation of the end effector 10 of the surgical instrument 50 will not be limited to the manners disclosed in the above mentioned embodiments of the invention, which can alternatively be performed in other manners. For example, Chinese patent application (with publication no. CN105433983A), entitled with "Articulation mechanism for a surgical instrument, and surgical instrument having the same" discloses another implementation for articulation of the end effector 10, which is hereby incorporated by reference in its entirety.

Figure 7:
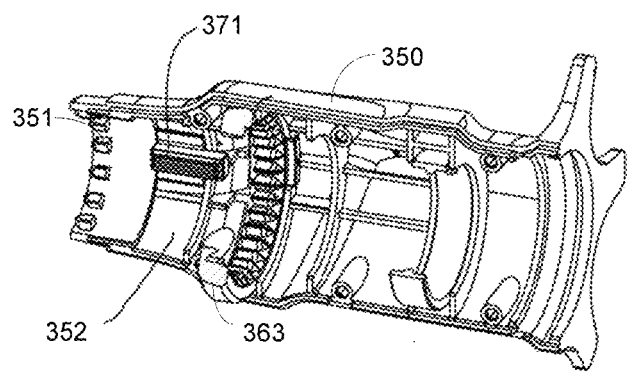
FIG. 7 is a schematic structural diagram of engagement between a slide member and a rotatable knob in the structure as illustrate in FIG. 2.

In order to switch the surgical instrument according to any one of the embodiments of the invention between rotation and articulation, and to prevent the surgical instrument from articulating during rotating, or from rotating during articulating, furthermore, a plurality of teeth 311 are arranged on the proximal portion of the rotatable sleeve 310, as illustrated in FIG. 2, the rotatable knob 350 can be operatively reciprocated in the longitudinal direction of the elongated portion 20. Correspondingly, a plurality of teeth 351 are arranged on the inner wall of the distal portion of the rotatable knob 350 (as illustrated in FIG. 7), configured to be engaged with the teeth 311 on the proximal portion of the rotatable sleeve 310. As illustrated in FIG. 2, when the rotatable knob 350 is located at its distal position, the teeth 351 on the distal portion of the rotatable knob 350 are meshed with the teeth 311 on the proximal portion of the rotatable sleeve 310, such that the rotatable sleeve 310 can be rotated as rotation of the rotatable knob 350 to thereby actuate the end effector 10 to rotate. The distal position where the rotatable knob 350 is located is also referred to as a rotation position. As illustrated in FIG. 3, when the rotatable knob 350 is located at the proximal position thereof, the teeth 351 on the distal portion of the rotatable knob 350 are disengaged from the teeth 311 on the proximal portion of the rotatable sleeve 310. Since the annular gear 363 of the articulation gear assembly 360 is fixedly mounted in the rotatable knob 350, as the rotatable knob 350 is moved to the proximal position thereof, the annular gear 363 is moved proximately therewith, so as to be engaged with the plurality of planet gears 362 of the articulation gear assembly 360. Rotating the rotatable knob 350, the annular gear 363 of the articulation gear assembly 360 is actuated to rotate therewith so as to articulate the end effector 10. The proximal position of where the rotatable knob 350 is located is also referred to as an articulation position.

Figure 6:
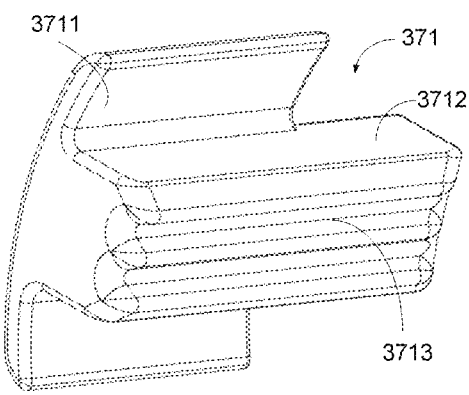
FIG. 6 is a schematic structural diagram of slide member of the surgical instrument according to the embodiment of the invention.
Figure 8:
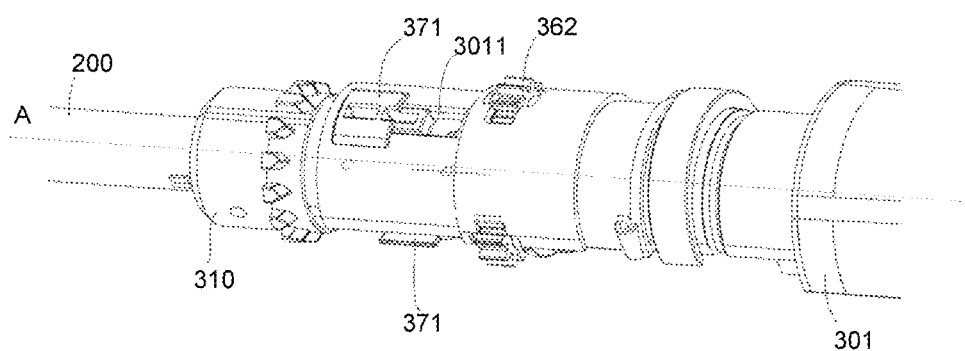
FIG. 8 is a schematic structural diagram of engagement between a slide member and a handle housing in the structure as illustrate in FIG. 2.

As can be apparent from the description above, when the rotatable knob 350 is located at the proximal position thereof, i.e., the articulation position, the teeth 351 on the distal portion of the rotatable knob 350 are disengaged from the teeth 311 on the proximal portion of the rotatable sleeve 310, so that rotation of the rotatable knob 350 can only actuate the end effector 10 to articulate rather than rotating. However, during surgeries, improper operations may cause some problems, for example, when the rotatable knob 350 is positioned at the articulation position for performing an articulating operation, the operator may accidently touch the rotatable sleeve 310 or the elongated portion 20 which may further actuate the end effector 10 to rotate. Based on the embodiment above of the invention, furthermore, as illustrated in FIG. 2 or FIG. 3, the surgical instrument 50 further includes a locking assembly 370 arranged in the rotatable knob 360, including at least one slide member 371 and a lockout gear 372, where the slide member 371 is arranged between the rotatable knob 350 and the distal end of the handle housing 301. Particularly as illustrated in FIG. 6, the slide member 371 is substantially designed as a T-shaped member, including a wing section 3711 and a cooperating section 3712. A plurality of transverse teeth 3713 are arranged on the bottom of the cooperating section 3712. Correspondingly as illustrated in FIG. 8, an elongated slot 3011 extending in the direction of the axis A is arranged on the distal portion of the handle housing 301, adapted to receive the cooperating section 3712 of the slide member 371 therein. Due to the elongated slot 301, the slide member 371 can only move axially (longitudinally) with respect to the handle housing 301, but biased circumferentially, that is, the slide member 371 can only slid in the elongated slot 3011 of the handle housing 301. Furthermore, an annular slot 352 configured to receive the wing section 3711 of the slide member 371 is arranged inside the rotatable knob 350, and for example, as illustrated in FIG. 7, the axial length of the annular slot 352 is equal to or slightly greater than that of the wing section 3711 of the slide member 371. The slide member 371 is axially biased in position by the annular slot 352 so that the slide member 371 cannot move axially (longitudinally) relative to the rotatable knob 350, that is, the slide member 371 moves together with the rotatable knob 350 proximately or distally.

Figure 9:
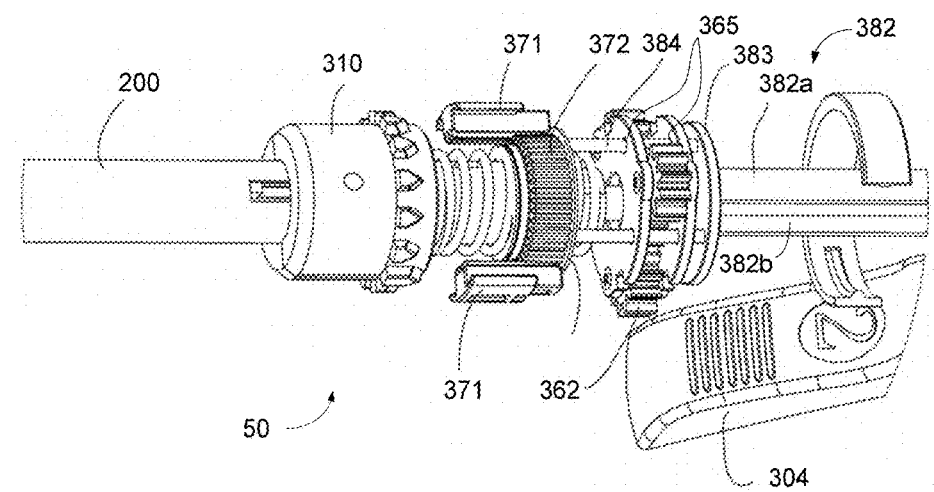
FIG. 9 is a schematic structural diagram of a part of a closure mechanism of the surgical instrument according to the embodiment of the invention.

The lockout gear 372 are sleeved on the proximal portion of the elongated body housing 200, and for example, the lockout gear 372 can be engaged with the elongated body housing 200 through a keyway and keys embedded therein. As illustrated in FIG. 2, FIG. 3, and FIG. 9, the lockout gear 372 is fixed with the elongated body housing 200, and a plurality of teeth are arranged on the lockout gear 372, configured to be engaged with the transverse teeth 3713 on the cooperating section 3712 of the slide member 371. In operation, when the rotatable knob 350 is located at the articulation position, as illustrated in FIG. 3, the transverse teeth 3713 of the slide member 371 are meshed with the lockout gear 372. Thus, during the rotation of the rotatable knob 350, the slide member 371 is fixed circumferentially in the elongated slot 3011 of the handle housing 301, which means it cannot be rotated together with the rotatable knob 350, and the lockout gear 372 meshed therewith cannot be rotated either, so that rotation of the end effector is not allowed while articulation operation is being performed.

Correspondingly, when the rotatable knob 350 moves distally, located at the rotation position, as illustrated in FIG. 2, the slide member 371 axially biased in position by the annular slot 352 of the rotatable knob 350 can move as the rotatable knob 350 is moving, that is, the slide member 371 moves distally together with the rotatable knob 350, so as to be disengaged from the lockout gear 372. Thus, rotation of the rotatable knob 350 actuates the rotatable sleeve 310 and the elongated portion 20 to rotate, and further actuates the end effector 10 to rotate.

In an alternative embodiment, further to the embodiment above, the locking assembly 370 of the surgical instrument 50 includes a plurality of slide members 371. Preferably, the plurality of slide members 371 are arranged on the distal portion of the handle housing 301, evenly spaced in circumferential direction thereof; and correspondingly a plurality of elongated slots 3011 are arranged on the distal portion of the handle housing 301, adapted to receive the corresponding slide members 371 respectively. Preferably, two slide members 371 are set, and two corresponding elongated slots 3011 are arranged on the distal portion of the handle housing 301.

Closure Mechanism

Figure 10:
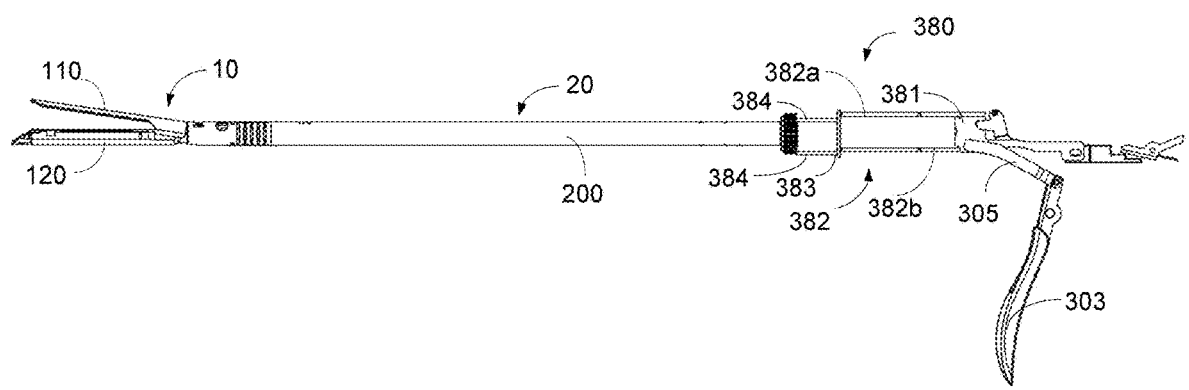
FIG. 10 is a schematic structural diagram of the closure mechanism of the surgical instrument according to the embodiment of the invention.

Referring to FIG. 10, the surgical instrument 50 according to the embodiment of the invention further includes a closure mechanism, where the closure mechanism includes a closure trigger 303, a transmission assembly 380 connected with the proximal end of the elongated body housing 200, and a linkage assembly 305, where a proximal end of the linkage assembly 305 is pivotally connected with the closure trigger 303, and a distal end thereof is pivotally connected with the transmission assembly 380. In order to further improve transmission stability, preferably the linkage assembly 305 includes a first link and a second link arranged in parallel to each other (not illustrated), which are pivotally connected respectively with ends of two sides of the closure trigger 303 (in the direction as illustrated in FIG. 10), and two sides of the proximal portion of the transmission assembly 380.

The distal portion of the transmission assembly 380 can be connected with the proximal portion of the elongated body housing 200 in various manners. For example, as illustrated in FIG. 10, the transmission assembly 380 preferably includes a connecting section 381 pivotally connected with the linkage assembly 305, and a connecting plate 382 rigidly connected with the distal end of the connecting section 381, and the distal end of the connecting section 381 is rigidly connected with the proximal end of the elongated body housing 200. Preferably, in order to provide more stable and reliable transmission of the transmission assembly 380, a plurality of connecting plates 382 can be provided, and for example, two connecting plates 382a and 382b can be arranged (as illustrated in FIG. 9).

Figure 11:
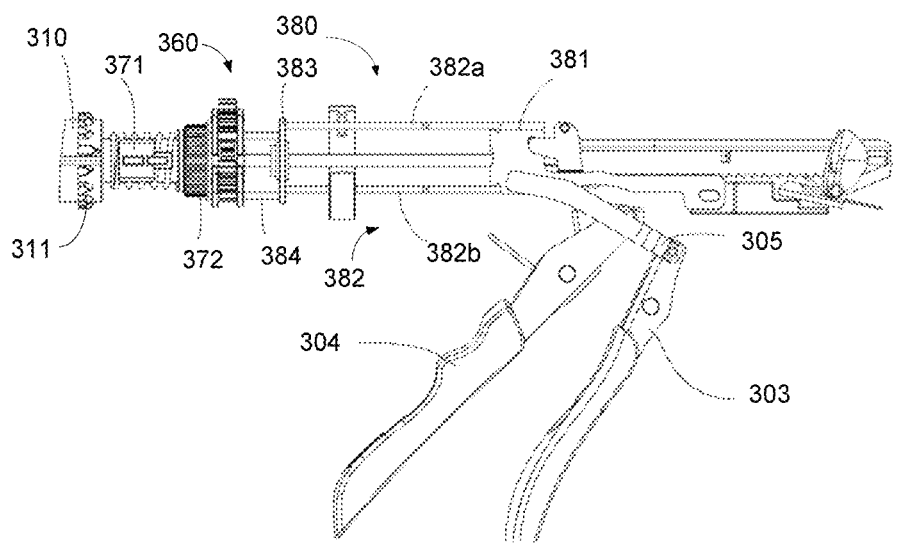
FIG. 11 is a schematic structural diagram of the closure mechanism of the surgical instrument according to the embodiment of the invention.
Figure 12:
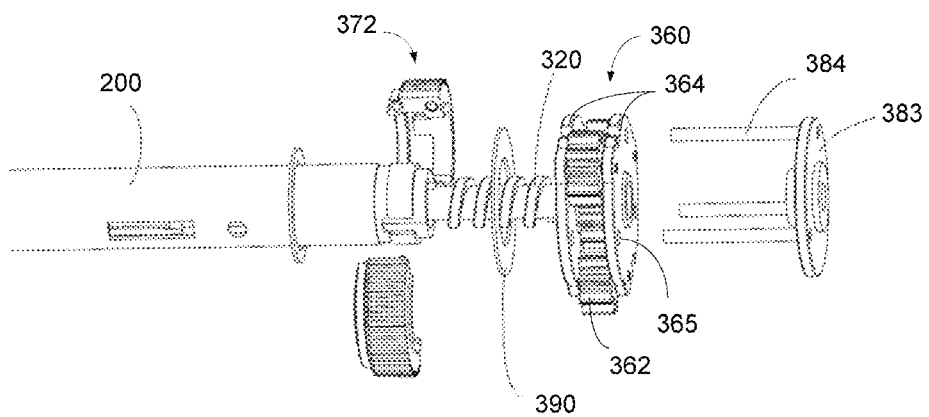
FIG. 12 is a schematic structural diagram of the closure lockout assembly in the surgical instrument according to the embodiment of the invention.

In order to facilitate rigid engagement between the distal end of the transmission assembly 380 and the proximal end of the elongated body housing 201, alternatively as illustrated in FIG. 11, it is preferred a push plate assembly including a push plate 383 and a plurality of push rods 384 is further arranged between the articulation gear assembly 360 and the connecting plate 382. The distal end of the connecting plate 382 is rigidly connected with the push plate 383, and a plurality of through-holes 364 are arranged on the articulation gear assembly 360, through which the push rods 384 can pass, as illustrated in FIG. 9 and FIG. 12, so that the push rods 384 can pass through the articulation gear assembly 360 so as to be engaged with the elongated body housing 200, or to be rigidly connected with the lockout gear 372. Since the lockout gear 372 is fixed with the proximal portion of the elongated body housing 200, the transmission assembly 380 is rigidly connected with the elongated body housing 201 as well.

During the operation, closing the closure trigger 303, the closure trigger 303 pivots counter-clockwise about the pivot thereof to thereby push the transmission assembly 380 through the linkage assembly 305 to the distal end thereof, and to further push the elongated body housing 200 to the distal end thereof so as to close the end effector 10.

It shall be noted that an implementation of the transmission assembly 380 can include but will not be limited to the implementation according to the embodiment above, but can alternatively be an implementation as commonly applied by those skilled in the art in the field of mechanics. For example, the connecting plate 382 of the transmission assembly 380 can alternatively be structured as a sleeve, a push bar, etc.

In order to further improve the safety of implementation of a surgical instrument, avoiding improper operations to the surgical instrument, further to the embodiments above, the surgical instrument 50 according to any one of the embodiments of the invention further includes a closure lockout assembly, configured to prevent the end effector 10 from being articulated and/or rotated after the end effector 10 of the surgical instrument 50 is closed. Particularly as illustrated in FIG. 12, a safety sheet 390 is further arranged between the lockout gear 372 and the articulation gear assembly 360, and preferably the safety sheet 390 is arranged as an annular sheet, where the proximal side of the annular sheet is fixed with the distal end of the push rod 383 of the transmission assembly 380 of the closure mechanism, thus while a closing operation is being performed, the transmission assembly 380 of the closure mechanism moves distally, pushing the safety sheet 390 to move distally therewith to further push the lockout gear 372 distally. Preferably, the outer diameter of the safety sheet 390 is slightly greater than the outer diameter of the lockout gear 372.

During operation, when the surgical instrument 50 is positioned at the rotation position, i.e. the rotatable knob 310 is positioned at the distal end thereof, and the end effector 10 is opened, where the slide member 371 is disengaged from the lockout gear 372, such that rotation of the end effector 10 is allowed. After the closure trigger 303 is closed, the transmission assembly 380 of the closure mechanism moves distally, actuating the safety sheet 390 to the distal end thereof, so as to push the lockout gear 372 distally therewith, and further to be engaged with the slide member 371, so that the surgical instrument 50 according to any one of the embodiments of the invention is not allowed to be rotated when the end effector 10 is closed.

Furthermore, when the surgical instrument 50 is positioned at the articulation position, that is, the rotatable knob 350 is at the distal end thereof, and the end effector 10 is opened, where the slide member 371 is engaged with the lockout gear 372, and the annular gear 363 of the articulation gear assembly 360 is engaged with the planet gear 362, so articulation of the end effector 10 is allowed. After closing the closure trigger 303, the transmission assembly 380 of the closure mechanism moves distally, actuating the safety sheet 390 to the distal end thereof. Since the outer diameter of the safety sheet 390 is slightly greater than the outer diameter of the lockout gear 372, and the lockout gear 372 can be pushed by the safety sheet 390 distally together with the slide member 371. Since the slide member 371 is axially fixed with the rotatable knob 310, as the slide member 371 is moving distally, it can actuate the rotatable knob 310 to the distal end thereof therewith, so that the annular gear 363 of the articulation gear assembly 360 is disengaged from the planet gear 362. Thus, the articulating operation function is disabled, so that articulation of the surgical instrument 50 according to any one of the embodiments of the invention is not allowed when the end effector 10 is closed.

In an alternative embodiment, the safety sheet 390 is structured integral to the lockout gear 372.

Figure 13:
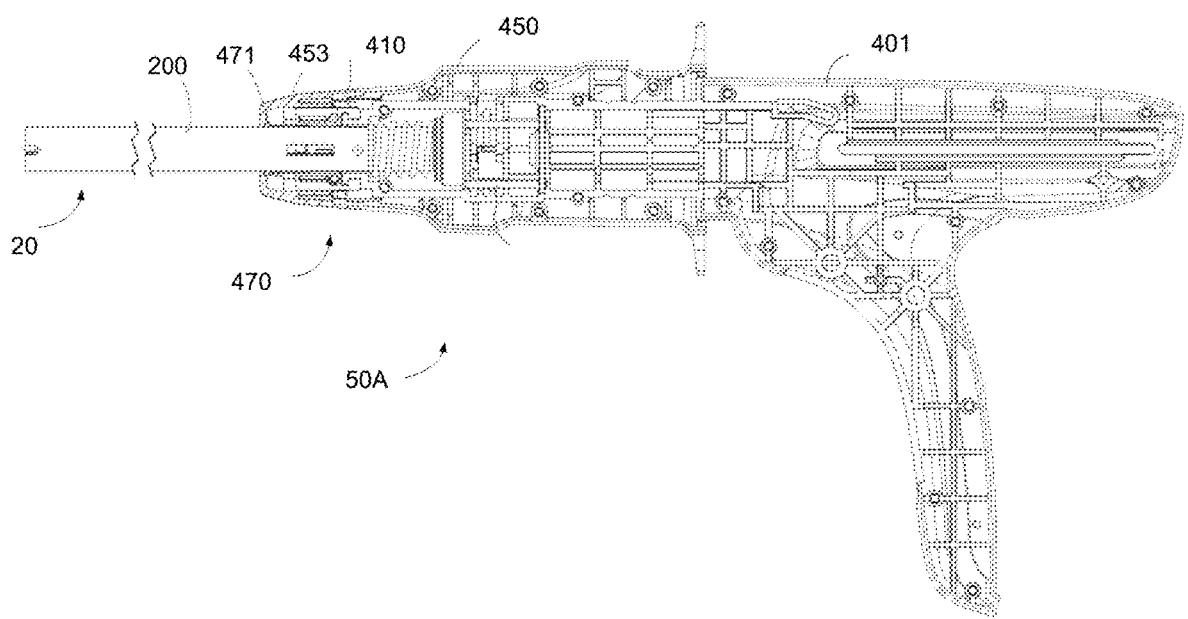
FIG. 13 is a schematic structural diagram of a handle portion of a surgical instrument according to another embodiment of the invention.
Figure 14:
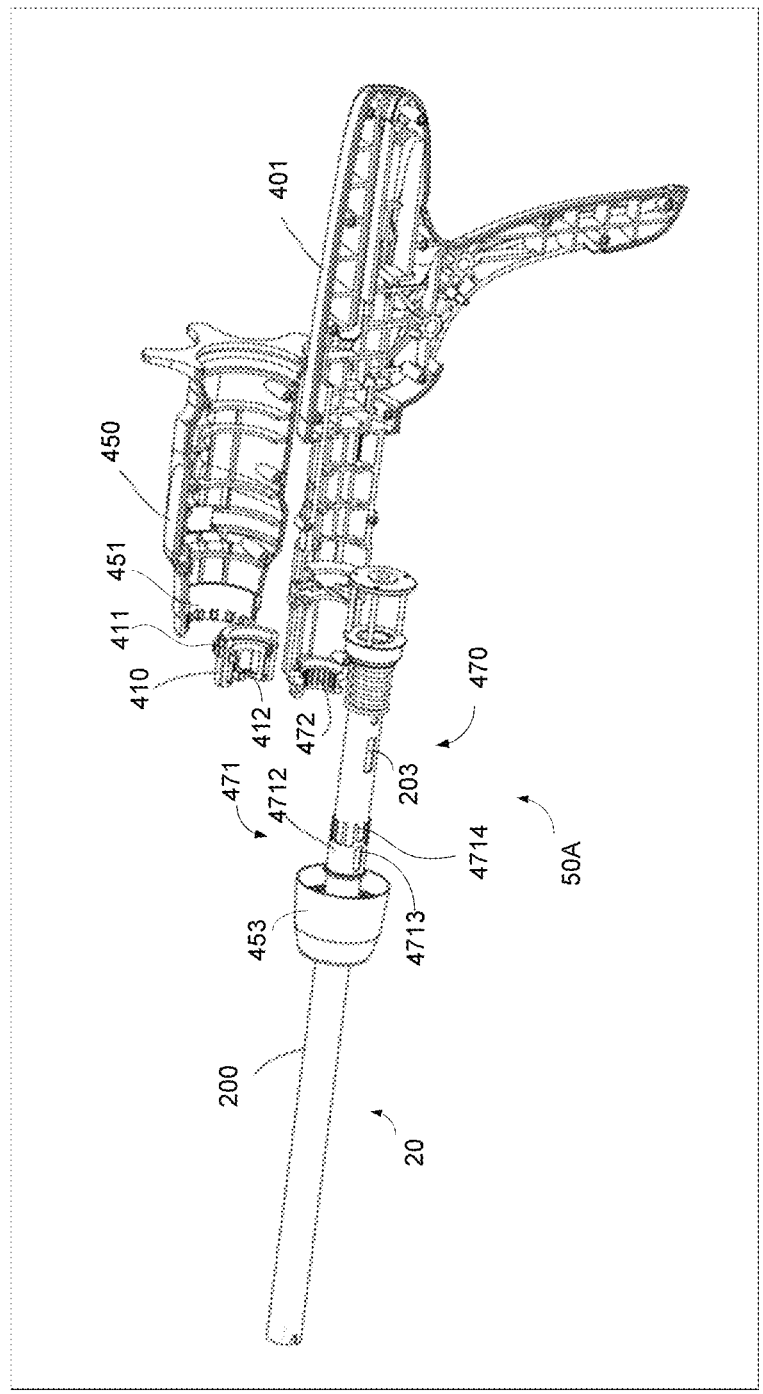
FIG. 14 is a schematic structural diagram of the handle portion in the surgical instrument in a decomposition view according to the other embodiment of the invention.
Figure 15:
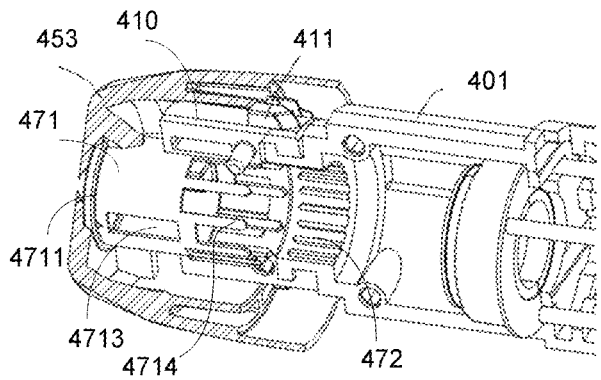
FIG. 15 is a schematic structural diagram of engagement between a slide member and a rotatable knob in the structure as illustrated in FIG. 14.
Figure 16:
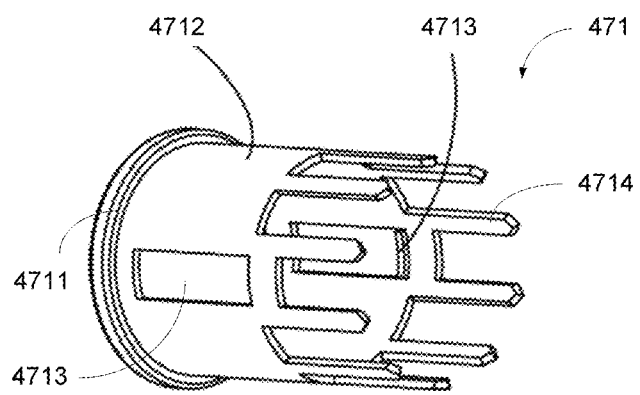
FIG. 16 is a schematic structural diagram of a slide member in the surgical instrument according to the other embodiment of the invention.

As an alternative embodiment, FIG. 13 illustrates an alternative of the surgical instrument 50 according to the embodiments above. As illustrated in FIG. 13, the surgical instrument 50A includes a rotatable knob 450, and a rotatable sleeve 410 arranged in the rotatable knob 450, where the rotatable sleeve 410 is rigidly connected with the elongated body housing 200 of the elongated portion 20, and the rotatable knob 450 can be operatively reciprocated relative to the elongated portion 20 in the longitudinal direction thereof. In order to facilitate assembling, preferably a head 453 of the rotatable knob 450 and the body of the rotatable knob are designed as two parts. A plurality of teeth 411 are arranged on the proximal portion of the rotatable sleeve 410, and a plurality of teeth 451 are correspondingly arranged on the inner wall of the rotatable knob 450, adapted to be engaged with the teeth 411 on the proximal portion of the rotatable sleeve 410. Particularly, when the rotatable knob 450 is positioned at the distal end thereof, i.e., a rotation position, the teeth 451 of the rotatable knob 450 are meshed with the teeth 411 of the rotatable sleeve 410, such that during the rotation of the rotatable knob 450, the rotatable sleeve 410 rotates therewith, actuating the elongated portion 20 and the end effector 10 to rotate. The surgical instrument 50A according to this embodiment includes the articulation mechanism of the surgical instrument 50 disclosed in the embodiment above, so explanation of how to articulate the instrument will be omitted here. When the rotatable knob 450 is positioned at the proximal end thereof, i.e., an articulation position, the teeth 451 of the rotatable knob 450 are disengaged from the teeth 411 of the rotatable sleeve 410. Since the annular gear of the articulation gear assembly (not illustrated) is fixedly mounted in the rotatable knob 450, as the rotatable knob 450 is moved to the proximal end thereof, the annular gear is moved proximately therewith, so as to be engaged with the plurality of planet gears of the articulation gear assembly. Rotating the rotatable knob 450, the annular gear of the articulation gear assembly is actuated to rotate therewith, to thereby articulate the end effector 10. Further to the embodiment above, referring to FIG. 13 and FIG. 14, the surgical instrument 50A further includes a locking assembly 470, arranged in the rotatable knob 450, including a slide member 471 and a lockout gear 472, where the slide member 471 is sleeved on the elongated body housing 200 of the elongated portion 20, and the lockout gear 472 is arranged on the distal portion of the handle housing 401. As illustrated in FIG. 15, a flange 4711 is arranged on the distal portion of the slide member 471, adapted to be snap-fit engaged with the distal end of the rotatable knob 450, that is, the flange 4711 is axially fixed with the rotatable knob 450 in snap-fit manner, circumferentially rotatable with respect to the rotatable knob 450. In addition, the slide member 471 can alternatively be axially fixed with the rotatable knob 450 in various common manners, e.g., using a slider and sliding slot.

As illustrated in FIG. 13 to FIG. 17, the slide member 471 further includes an annular portion 4712 extending from the flange 4711 to the proximal end thereof, and at least one positioning slot 4713 is arranged on the annular portion 4712; and correspondingly at least one elongated slot 203 is arranged on the elongated body housing 200, and at least one protrusion 412 is arranged on the inside of the rotatable sleeve 410, so that the protrusion 412 of the rotatable sleeve 410 runs through the positioning slot 4713 of the slide member 471, and the elongated slot 203 of the elongated body housing 200, and thus the slide member 471, the elongated body housing 200, and the rotatable sleeve 410 can axially move relative to each other while being biased circumferentially. Furthermore the slide member 471 further includes a plurality of teeth 4713, extending from the annular portion 4712 to the proximal end thereof, adapted to be engaged with the lockout gear 472 on the distal portion of the handle housing 401.

Particularly when the rotatable knob 450 is positioned at the rotation position, the slide member 471 together with the rotatable knob 450 are positioned at the distal end, where the teeth 4713 on the proximal portion of the slide member 471 are disengaged from the lockout gear 472, so that rotation of the rotatable knob 450 actuates the rotatable sleeve 410, the elongated portion 20 and the end effector 10 to rotate therewith, so as to actuate the annular gear 463 to be disengaged from the planet gear 462, disabling articulation of the instrument. When the rotatable knob 450 moved proximately to so as to be positioned at the articulation position, the slide member 471 is actuated by the rotatable knob 450 to the proximal end thereof, so that the teeth 4713 of the slide member 471 are engaged with the lockout gear 472, and thus as the rotatable knob 450 is rotating, the slide member 471 is biased circumferentially, and thus cannot be rotated together with the rotatable knob 450, thus rotation is not allowed while performing an articulating operation.

Figure 17:
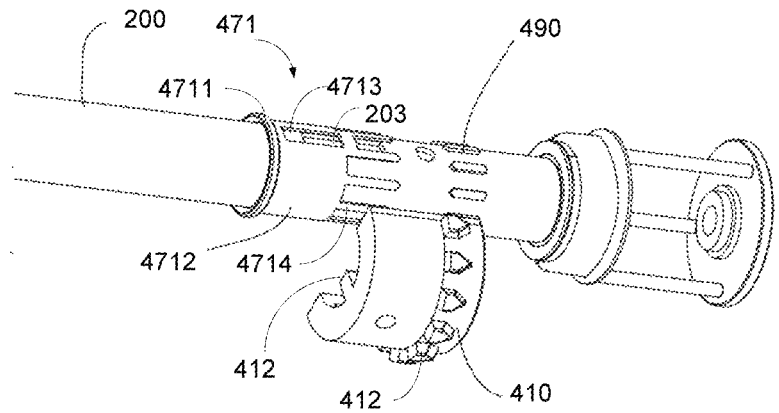
FIG. 17 is a schematic structural diagram of a slide member and a closure lockout assembly in the surgical instrument according to the other embodiment of the invention.

Furthermore, it is provided in the embodiment the surgical instrument 50A includes the closure mechanism of the surgical instrument 50 disclosed in the above embodiments for closing or opening the end effector 10. The closure lockout assembly includes a plurality of closure lockout teeth 490 arranged on the elongated body housing 200. Particularly, as illustrated in FIG. 17, a plurality of closure lockout teeth 490 are arranged between the proximal portion of the elongated body housing 200, and the slide member 471, and distal ends thereof are aligned with the proximal ends of the teeth 4713 of the slide member 471.

Figure 18:
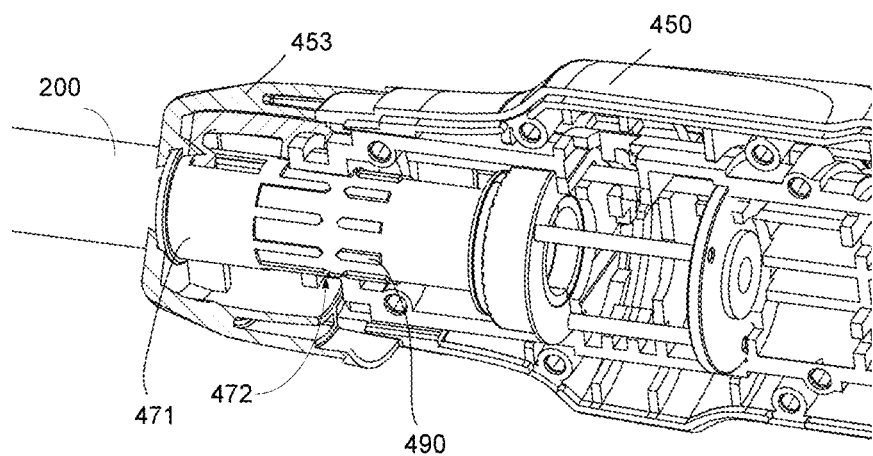
FIG. 18 is a schematic structural diagram after the surgical instrument is closed at a rotation position according to the other embodiment of the invention.

During operation, when the surgical instrument 50A is positioned at the rotation position, that is, the rotatable knob 450 is positioned at the distal end thereof, as well as the end effector 10 is open, where the slide member 471 is disengaged with the lockout gear 472, and rotation of the end effector 10 is allowed. After the closure trigger 303 is closed, the closure mechanism 380 moves distally, pushing the elongated body housing 200 of the elongated portion 20 distally, and the closure lockout teeth 490 arranged on the elongated body housing 200 move distally therewith, so that the surgical instrument 50A according to this embodiment cannot perform any rotation operation when the end effector 10 is closed as illustrated in FIG. 18.

Figure 19:
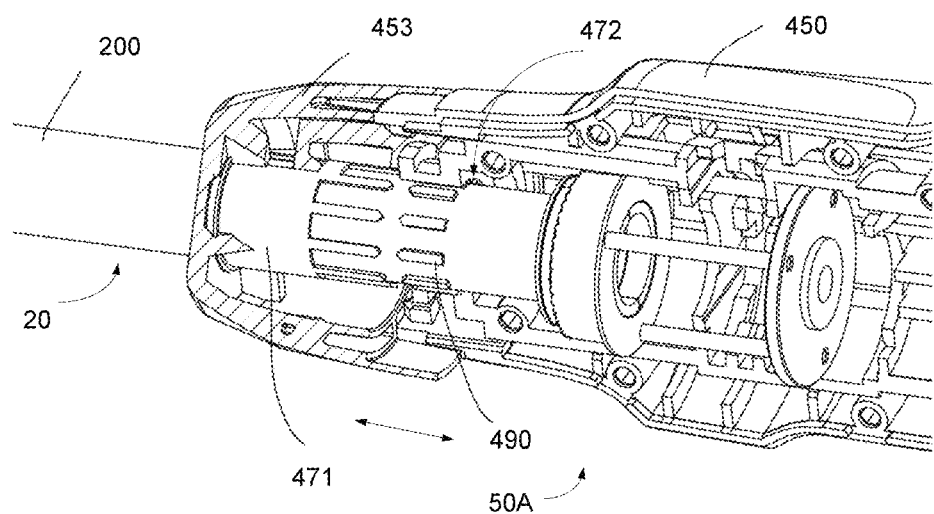
FIG. 19 is a schematic structural diagram after the surgical instrument is closed at an articulation position according to the other embodiment of the invention.

When the surgical instrument 50A is positioned at the articulation position, that is, the rotatable knob 450 is positioned at the proximal end thereof, as well as the end effector 10 is open, where the slide member 471 is engaged with the lockout gear 472, and the annular gear 463 of the articulation gear assembly 460 is engaged with the planet gear 462, and articulation of the end effector 10 is allowed. After the closure trigger 303 is closed, the closure mechanism moves distally, actuating the elongated body housing 200 of the elongated portion 20 to move distally. Since the closure lockout teeth 490 arranged on the elongated body housing 200 are aligned with the teeth 4713 of the slide member 471, as the closure lockout teeth 490 are moving distally together with the elongated body housing 200, the slide member 471 is pushed distally so as to actuate the rotatable knob 450 to the distal end, so that the annular gear 463 is disengaged from the planet gear 462, and the closure lockout teeth 490 are engaged with the lockout gear 472 as well. As illustrated in FIG. 19, neither articulation nor rotation of the surgical instrument 500 according to this embodiment is allowed when the end effector 10 is closed.

It shall be noted that the numbers of teeth of the slide member 471, the lockout gear 472, and the closure lockout tooth 490 in the surgical instrument 50A according to the embodiment of the invention will not be limited to any particular numbers as long as they can be engaged with each other as described in the embodiment above.

In the locking assembly above, the respective components are transmission-connected and engaged with each other in a mechanical manner, so as to provide stable engagements.

Those skilled in the art can make various modifications and variations to the invention without departing from the spirit and scope of this disclosure. Thus the invention is also intended to encompass these modifications and variations thereto so long as the modifications and variations come into the scope of the claims appended to the invention and their equivalents.

The invention claimed is:

1. A surgical instrument, comprising:
   a handle portion having a handle housing;
   an elongated body, defining a longitudinal axis of the instrument;
   an end effector, arranged on distal portion of the elongated body for operating tissues;
   a rotatable sleeve, circumferentially fixed with proximal portion of the elongated body and provided with a plurality of teeth;
   a rotatable knob, operatively to be reciprocated along the longitudinal axis, wherein the rotatable knob is provided with a plurality of teeth for operatively engaged with the teeth of the rotatable sleeve in distal position thereof; and
   an articulation gear assembly comprising an annular gear and a planet gear assembly, wherein the annular gear that is rigidly amounted with the rotatable knob, and operatively engaged with the planet gear when the rotatable knob is operated in proximal position thereof.

2. The surgical instrument according to claim 1, further comprising a driving screw rigidly connected with a sun gear of the articulation gear assembly;
   wherein the driving screw comprises a thread section that is engaged with a driving rod assembly coupled to the end effector.

3. The surgical instrument according to claim 2, wherein the thread section of the driving screw is provided with at least two opposing threads that are engaged with respective driving rods of the driving rod assembly, such that when the rotatable knob is operated in proximal position thereof, rotating the rotatable knob articulates the end effector.

4. The surgical instrument according to claim 1, further comprising a locking assembly comprising at least one slide member and a lockout gear;

wherein the slide member is arranged between the rotatable knob and the handle housing, and axially fixed with the rotatable knob, so as to be reciprocated with the rotatable knob for being operatively engaged with the lockout gear; and the slide member is circumferentially fixed with the handle housing; and the lockout gear is rigidly mounted at a proximal portion of the elongated portion.

5. The surgical instrument according to claim 4, wherein the slide member is axially fixed in the rotatable knob and configured to be rotatable with respect to the rotatable knob.

6. The surgical instrument according to claim 5, wherein the rotatable knob further comprises an annular slot configured to receive the slide member, allowing the slide member to move circumferentially therein.

7. The surgical instrument according to claim 5, wherein an elongated slot is arranged in the distal portion of the handle housing of the handle portion to prevent the slide member from moving circumferentially.

8. The surgical instrument according to claim 4, wherein the rotatable knob is provided with two, three, or four slide members that are evenly spaced in the circumferential direction thereof.

9. The surgical instrument according to claim 1, wherein the handle portion further comprises a stationary handle and a closure trigger; and the closure trigger is pivotally mounted on the handle housing, and connected with a closure mechanism arranged in the handle housing, configured for actuating the elongated portion through the closure mechanism to reciprocate for opening or closing the end effector.

10. The surgical instrument according to claim 9, wherein the handle portion further comprises a closure lockout assembly rigidly engaged with the closure mechanism; and when the closure trigger is closed, the closure lockout assembly is operatively pushed distally by the closure mechanism.

11. The surgical instrument according to claim 10, wherein the closure lockout assembly is arranged as a safety sheet arranged between the lockout gear and the articulation gear assembly; and as the safety sheet is moving distally, the safety sheet pushes the lockout gear to move distally; or as the safety sheet is moving distally, the safety sheet pushes the lockout gear and the slide member to move distally.

12. The surgical instrument according to claim 11, wherein the safety sheet is structured integral to the articulation gear assembly.

13. The surgical instrument according to claim 11, wherein the safety sheet is arranged as an annular sheet, the outer diameter of which is greater than the outer diameter of the lockout gear.

14. The surgical instrument according to claim 1, further comprising a locking assembly comprising a slide member and a lockout gear;

wherein the slide member is arranged between the rotatable knob and the handle housing, and axially fixed with the rotatable knob, for being reciprocated with the rotatable knob to be operatively engaged with the lockout gear;

the slide member is circumferentially fixed with the elongated portion; and the lockout gear is fixedly mounted in the handle housing.

15. The surgical instrument according to claim 14, wherein the slide member is fixedly sleeved circumferentially on a proximal portion of the elongated portion; and a flange is arranged on a distal portion of the slide member to be snap-fit engaged with the rotatable knob.

16. The surgical instrument according to claim 15, wherein a plurality of teeth are arranged on a proximal portion of the slide member, and as the slide member is moved to the proximal end, the slide member is operatively engaged with the lockout gear.

17. The surgical instrument according to claim 14, wherein the lockout gear is fixedly arranged on the distal portion of the handle housing of the handle portion.

18. The surgical instrument according to claim 14, wherein the handle portion further comprises a rotatable sleeve arranged on a distal portion thereof, and rigidly connected with the elongated portion;

wherein the rotatable knob is operatively engaged with the rotatable sleeve; and a plurality of teeth are arranged respectively on the rotatable sleeve and the rotatable knob, through which the rotatable knob is operatively engaged with the rotatable sleeve.

* * * * *